United States Patent
Bischoff et al.

(10) Patent No.: US 8,292,432 B2
(45) Date of Patent: Oct. 23, 2012

(54) OPHTHALMIC APPARATUS AND OPHTHALMIC METHOD FOR POSITIONING AN EYE OF A PATIENT IN A PREDETERMINED NOMINAL POSITION

(75) Inventors: Mark Bischoff, Jena (DE); Gregor Stobrawa, Jena (DE)

(73) Assignee: Carl Zeiss Meditec AG, Jena (DE)

(*) Notice: Subject to any disclaimer, the term of this patent is extended or adjusted under 35 U.S.C. 154(b) by 616 days.

(21) Appl. No.: 12/513,767

(22) PCT Filed: Oct. 29, 2007

(86) PCT No.: PCT/EP2007/009376
§ 371 (c)(1),
(2), (4) Date: May 6, 2009

(87) PCT Pub. No.: WO2008/055604
PCT Pub. Date: May 15, 2008

(65) Prior Publication Data
US 2010/0026956 A1    Feb. 4, 2010

Related U.S. Application Data

(60) Provisional application No. 60/865,222, filed on Nov. 10, 2006.

(30) Foreign Application Priority Data

Nov. 10, 2006  (DE) .......................... 10 2006 053 098

(51) Int. Cl.
*A61B 3/14* (2006.01)

(52) U.S. Cl. .......................... 351/206; 351/219; 351/246

(58) Field of Classification Search .................. 351/200, 351/205–206, 246, 219
See application file for complete search history.

(56) References Cited

U.S. PATENT DOCUMENTS

| | | | |
|---|---|---|---|
| 4,838,682 A | 6/1989 | Portnoy | |
| 5,469,234 A | 11/1995 | Konishi | |
| 7,284,858 B2 | 10/2007 | Bergner | |
| 2004/0044333 A1 | 3/2004 | Sugiura | |
| 2004/0143246 A1 | 7/2004 | Maeda et al. | |
| 2006/0192921 A1* | 8/2006 | Loesel et al. .................. | 351/219 |
| 2007/0225693 A1 | 9/2007 | Muehlhoff et al. | |

(Continued)

FOREIGN PATENT DOCUMENTS

DE    10 2005 001 249 A1    7/2006

(Continued)

*Primary Examiner* — James Greece
(74) *Attorney, Agent, or Firm* — Patterson Thuente Christensen Pedersen, P.A.

(57) ABSTRACT

An ophthalmic apparatus including a supporting device for a patient and an eye treatment device. The apparatus includes a contact element for spatially fixing an eye of the patient with respect to the treatment device, and a positioning device for shifting the supporting device and a contact element relative to each other in order to position the eye, before it is fixed using the contact element, at a predetermined nominal position relative to the contact elements. The ophthalmic apparatus includes a detection device, which records an image of the eye of the patient present on the supporting device and, on the basis of said recorded image, determines an indication concerning a relative shift of the supporting device with respect to the contact element, which shift is required to move the eye to the nominal position by means of the positioning device.

16 Claims, 4 Drawing Sheets

U.S. PATENT DOCUMENTS

2008/0243107 A1  10/2008  Muhlhoff et al.

FOREIGN PATENT DOCUMENTS

| | | | |
|---|---|---|---|
| EP | 0 765 648 | A2 | 4/1997 |
| EP | 1 316 287 | A2 | 6/2003 |
| WO | WO 02/065899 | A2 | 8/2002 |
| WO | WO 2006/074898 | A1 | 7/2006 |

\* cited by examiner

OPHTHALMIC APPARATUS AND OPHTHALMIC METHOD FOR POSITIONING AN EYE OF A PATIENT IN A PREDETERMINED NOMINAL POSITION

PRIORITY CLAIM

The present application is a National Phase Entry of PCT Application No. PCT/EP2007/009376, filed Oct. 29, 2007, which claims priority to U.S. Provisional Application No. 60/865,222, filed Nov. 10, 2006, and German Application Number 102006053098.5, filed Nov. 10, 2006, the disclosures of which are hereby incorporated by reference herein in their entirety.

FIELD OF THE INVENTION

The invention relates to an ophthalmic apparatus, in particular for contacting therapeutic methods, such as, for example, femtosecond laser treatments, said apparatus comprising a supporting device for a patient, an eye treatment device comprising a contact element for spatially fixing an eye of the patient with respect to the treatment device, and a positioning device for shifting the supporting device and the contact element relative to each other, so as to position the eye in a predetermined nominal position relative to the contact element before the eye is fixed using the contact element. Further, the invention relates to an ophthalmic method for positioning an eye of a patient in a predetermined nominal position.

BACKGROUND OF THE INVENTION

These therapeutic methods require precise spatial approximation and coupling of a patient's eye and the treatment device. In order to move the patient or the eye of the patient, respectively, into the correct position relative to the contact element, the operator (or the physician, respectively) used to effect positioning completely manually. This requires great experience and a corresponding manual dexterity.

SUMMARY OF THE INVENTION

In view thereof, it is an object of the invention to improve an ophthalmic apparatus of the above-mentioned type such that positioning of the eye at the nominal position can be effected in a simple and precise manner.

According to the invention, this object is achieved by an ophthalmic apparatus of the above-mentioned type, wherein a detection device is provided, which records an image of the eye of the patient present on the supporting device (before the contact element fixes the patient's eye) and, on the basis of said recorded image, determines an indication concerning a relative shift of the supporting device with respect to the contact element, which shift is required in order to move the eye to the nominal position by means of the positioning device.

The determined indication may be provided, for example, to the operator of the apparatus, such that the operator knows how to control the positioning device in order to move the eye to the nominal position. As an alternative, it is possible to effect said positioning automatically on the basis of said indication.

Said indication may be, for example, an indication of direction, which indicates in which direction the relative shift is to be carried out. It is also possible that the indication is the absolute relative shift itself.

Said indication can be provided to the operator by visual and/or acoustic means.

The nominal position is a desired position and/or orientation of the patient's eye relative to the contact element, wherein, in particular, the position of the contact element relative to optics of the treatment device is defined or determined, respectively. The nominal position can be, for example, a predetermined orientation of the axis of vision of the eye and/or predetermined positioning of the pupil of the eye relative to the contact element.

The detection device can determine the indication concerning the relative shift and the remaining relative shift by determining the actual position of the eye on the basis of the recorded image of the eye, comparing the actual position with the nominal position, calculating the required shift therefrom and deriving the indication from the required shift.

The supporting device can be provided, for example, as a bed or as a chair.

The detection device can produce another recorded image of the eye during or after a shift caused by the positioning device or during or after part of such shift and can determine, on the basis of the further recorded image, an indication concerning a remaining relative shift of the supporting device relative to the contact element, which shift is required in order to move the eye to the nominal position by means of the positioning device. Thus, it is possible to effect positioning automatically. In particular, a closed-loop circuit can thus be provided by which positioning can be carried out automatically in a simple and precise manner.

The positioning device can cause a relative shift of the supporting device with respect to the contact element (and thus, the treatment device) on the basis of the determined indication(s). This allows automatic positioning to be realized.

In particular, it is possible that the positioning device will cause shifting while the contact element is in contact with the eye. In this case, there is already a contact, but the contact element does not yet fix the eye in space. Thus, a very good fine adjustment of positioning can be realized, so that high-precision positioning can be realized.

In particular, the apparatus may comprise a signaling unit signaling to an operator of the ophthalmic apparatus, on the basis of the determined indication(s), how to control the positioning device in order to move the eye to the nominal position. This achieves a combination of manual positioning and automatic positioning. The operator is advantageously assisted by the detection device in positioning the eye relative to the contact element or to the treatment device, respectively.

On the basis of the eye pupil's position in the recorded image, the detection device can determine the indication concerning the relative shift or the remaining relative shift, respectively. Thus, for example, edge recognition can be carried out. Such edge recognition is described, for example, in WO 02/065899 A2. Any other type of determination of the shape and/or position of the pupil can be used.

Further, it is also possible to evaluate any other suitable structure of the eye in the recorded image for positioning.

The treatment apparatus can spatially fix the eye, located at the nominal position, by means of the contact element.

After fixation, a desired treatment can then be carried out. In particular, the eye treatment device can comprise a laser, such as, for example, a femtosecond laser. The desired treatment may be, for example, the correction of an eyesight defect or ametropia.

The detection device may be provided such that it determines the required relative shift in one, two or three dimensions. Preferably, it determines the required shift in two dimensions. In particular, a plane is selected for this purpose, which is located substantially perpendicular to the axis of vision of the patient on the supporting device. The plane can also be located substantially perpendicular to the beam direction of a laser for treatment of the eye, said laser being part of the treatment device. The positioning along the axis of vision or the setting of the distance between the contact element and the eye, respectively, for contacting the eye with the contact element can then be carried out manually by the operator of the ophthalmic apparatus.

The ophthalmic apparatus may comprise one or more sensors, to detect the contact between the contact element and the eye. In particular, the sensor(s) can be used to prevent inadvertent contacting and to control deliberate contacting such that the patient's eye is not damaged. The sensor(s) may be of the pressure sensor-type which detects the contact pressure of the eye on the contact element.

The contact element may be provided as a contact glass whose side facing the patient's eye is curved (for example spherically curved) and whose side facing away from the patient's side is planar. By the curved contact side facing towards the eye, it is well possible to displace the contact element relative to the eye, if there already is a contact between the contact element and the eye, but the contact element does not yet spatially fix the eye.

In one embodiment, recording an image of the eye is effected through the contact element.

Further, the detection device may also comprise a source of illumination, which emits illumination radiation used to record an image of the eye. The illumination radiation may be radiation in the visible wavelength range or may be radiation from the infrared wavelength range.

The detection device may further be provided such that it first determines, on the basis of the recorded image, whether the eye is located within a predetermined capturing region, within which the indication concerning the required relative shift can be determined. If this is not the case, the detection device will output a corresponding message, so that the operator can position the patient manually such that the patient's eye is located within the predetermined capturing region.

The detection device can record an image of the eye by means of optical imaging. In particular, the detection device can generate an image of the eye (for example, by means of a camera).

However, the recorded image can also be prepared in any other way, provided that information concerning the actual position of the eye can be derived from such recorded image.

The relative shift of the supporting device with respect to the contact element can be effected by displacing the supporting device, the contact element or the supporting device and the contact element together.

In one embodiment, the contact element is releasably connected with the optics of the treatment device and can be realized as a part for one-time use, which is disposed of after use for a patient and replaced by a new contact element of the same construction for a further patient.

The detection device can communicate with the supporting device via a wire connection or a wireless connection.

There is further provided an ophthalmic method for positioning an eye of a patient at a predetermined nominal position relative to a contact element of an eye treatment device, wherein the eye of the patient is recorded and, on the basis of the recorded image, an indication concerning a relative shift of the patient with respect to the contact element is determined, said shift being required to move the eye to the nominal position, and wherein, on the basis of said indication, the required relative shift is effected or the indication is provided to an operator of the eye treatment device.

Using this method, precise positioning of the eye is easily possible.

In particular, a further recorded image of the eye can be made during or after the required relative shift or part thereof, and an indication concerning a remaining relative shift of the patient with respect to the contact element can be determined, said shift being required to move the eye to the nominal position, and on the basis of said indication concerning the remaining relative shift, the remaining relative shift can be effected or the indication concerning the remaining relative shift can be provided to an operator of the treatment device. This increases the precision of positioning.

In the method, shifting can be effected while the contact element of the treatment device is in contact with the eye. This enables fine adjustment prior to final fixation.

Said method allows signaling to an operator, on the basis of the determined indication(s), how a positioning device for shifting the patient and the contact element relative to each other is to be controlled in order to move the eye to the nominal position.

Further, the eye located at the nominal position can be spatially fixed and, following said fixation step, the desired eye treatment can be carried out.

In particular, the indication concerning the relative shift or the remaining relative shift, respectively, can be determined on the basis of the position of the eye pupil in the recorded image.

Further, the ophthalmic apparatus can be provided such that the described method and/or its further embodiments can be carried out by said apparatus.

It is evident that the above-mentioned features and the features to be explained hereinafter can be used not only in the combinations mentioned, but also in other combinations, or alone, without departing from the scope of the invention.

BRIEF DESCRIPTION OF THE DRAWINGS

The invention will be explained in more detail below, by way of example and with reference to the drawings, which also discloses essential features of the invention. In the drawings.

DETAILED DESCRIPTION

Figure 1:
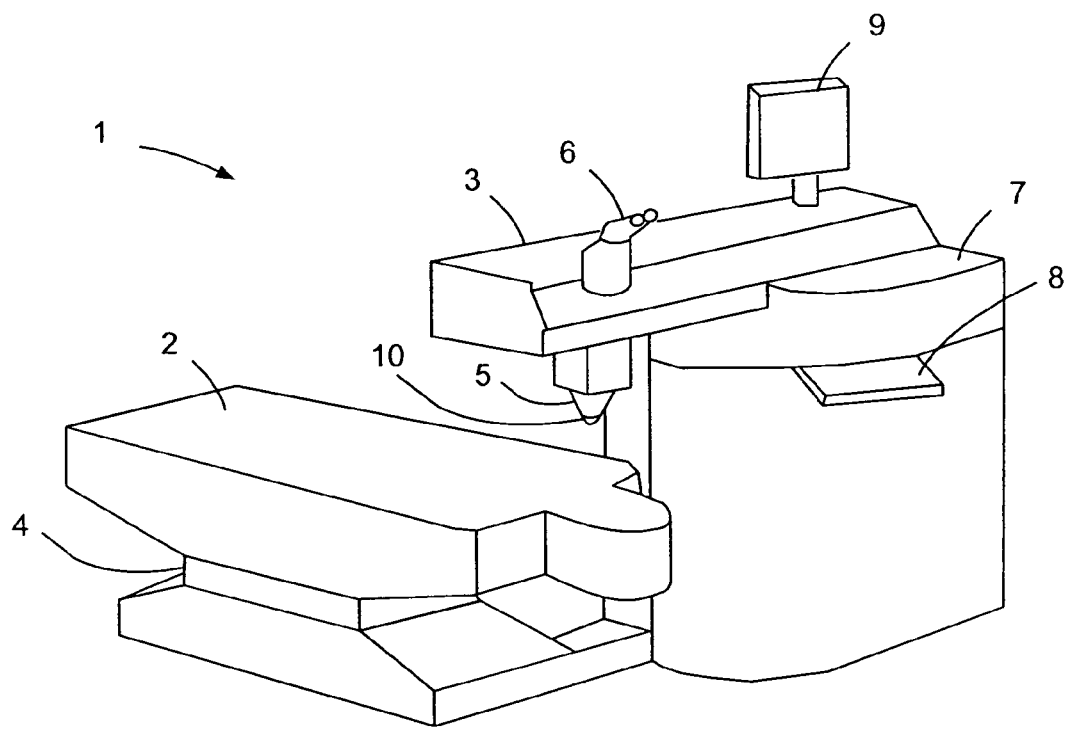
FIG. 1 shows a schematic perspective view of an embodiment of the ophthalmic apparatus.

In the embodiment shown in FIG. 1, the ophthalmic apparatus 1 according to the invention serves to correct an eyesight defect using laser radiation and comprises a supporting device 2 for a patient in the form of a bed, an eye treatment device 3, as well as a positioning device 4 carrying the bed 2 and allowing its movement in all three spatial directions.

The treatment device 3 comprises a treating head 5, arranged above the bed 2, as well as a microscope ocular 6, by which a surgeon can follow the progress of treatment. Further, the treatment device 3 comprises a computer 7 including a keyboard 8 and a monitor 9. The ophthalmic apparatus 1 is controlled by means of the computer 7.

The treating head 5 comprises, at its end facing the bed 2, a contact element 10 in the form of a contact glass which contacts the patient's eye during treatment and fixes it in space relative to the treatment device 3 and through which the treatment laser radiation is focused in the patient's eye.

In order to be able to carry out the positioning of the patient's eye relative to the contact glass 10, before the contact glass 10 spatially fixes the patient's eye, for example by suction, in a simple and precise manner, a detection device 11 (FIG. 2) is provided.

Figure 2:
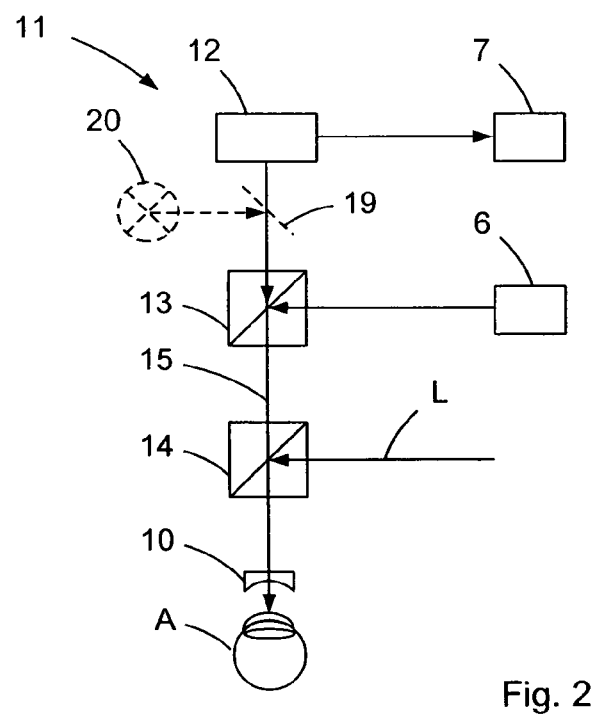
FIG. 2 shows a schematic representation of a detection device of the ophthalmic apparatus according to FIG. 1.

In FIG. 2, the detection device 11, which is arranged inside the housing of the treatment device 3, is shown schematically and strongly simplified with respect to the optical construction, said detection device 11 comprising a camera 12 by which the eye A of the patient is recorded through two beam splitters 13, 14 and the contact glass 10, which is still at a distance from the eye A. Thus, an observation beam path 15 extends from the camera 12 to the eye A through both beam splitters 13 and 14 as well as the contact glass 10. The image recorded by the camera 12 is transmitted to the computer 7.

The beam splitter 13 serves to allow observations of the eye A through the microscope ocular 6. Treatment laser radiation L is directed to the eye A via the beam splitter 14, if said eye A is spatially fixed by means of the contact glass 10 so as to effect the correction of defective eyesight desired here.

The recorded image of the eye A is evaluated in the computer 7 to allow control of the positioning device 4 such that the bed 2 and, thus, the eye A of the patient present on the bed 2 can be moved to a predetermined nominal position relative to the contact glass 10.

Figure 3:
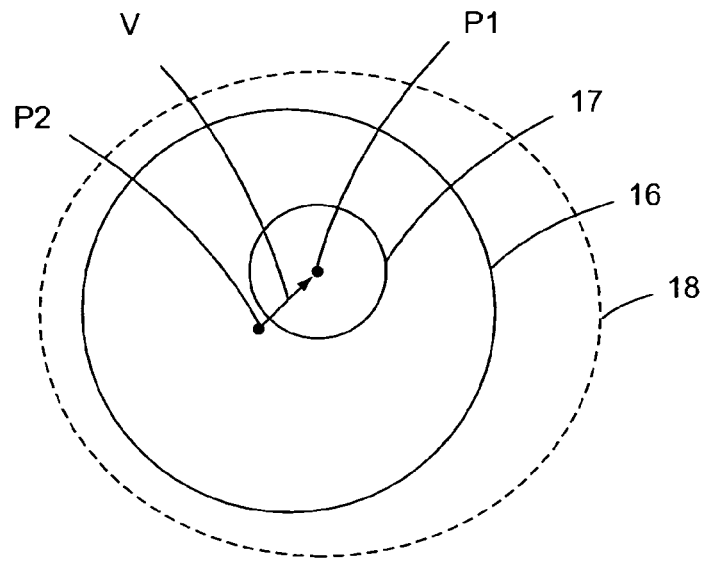
FIG. 3 shows a view of a recorded image of a patient's eye.

In the presently described embodiment, the position of the eye pupil in the recorded image is determined for this purpose. By a comparison with nominal data, the required shift can then be determined. FIG. 3 schematically shows a recorded eye A, wherein the iris 16 as well as the eye pupil 17 are indicated. Further, the center of the pupil is referred to as P1 and the nominal position of the pupil's center is referred to as P2.

As is evident from the representation of FIG. 3, the pupil's center P1 is shifted with respect to the nominal position P2. Said shift is schematically shown by the shifting vector V. The computer 7 can, thus, determine the shifting vector V by a comparison of the position of the pupil's center P1 with the nominal position P2 and derive therefrom the required control signal for the positioning device 4. In the representation of FIG. 3, it was assumed that shifting is required only in a plane parallel to the bed and, thus, substantially perpendicular to the observation beam path 15; setting the distance between the contact glass and the eye A can be effected manually by the surgeon, with visual control via the microscope ocular 6.

When the eye A is at the nominal position, the contact glass 10 is placed on the eye and then spatial fixation is effected, for example, by suction. The lower side of the contact glass 10 facing the eye A may be curved (e.g. spherically). The upper side of the contact glass facing away from the eye A is preferably planar.

In a modification of the above-described embodiment, it is also possible to effect shifting, if its amount is not too great, when the contact glass 10 is already in contact with the eye A (but no spatial fixation is present, for example, by suction). This allows extremely exact and precise positioning.

Figure 4:
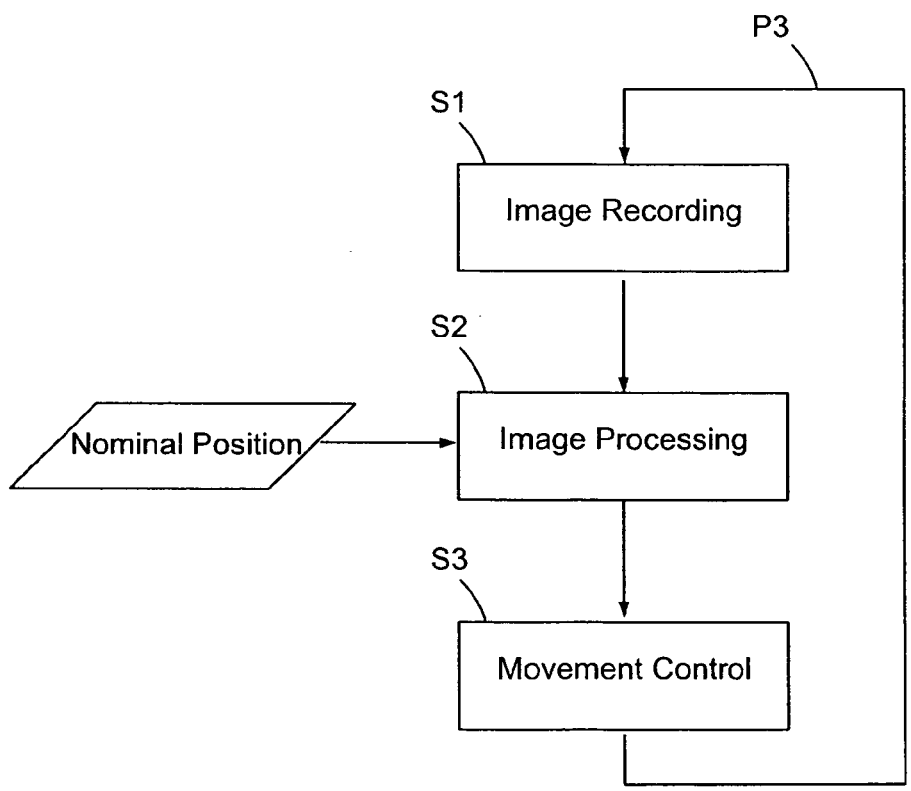
FIG. 4 shows a flow scheme explaining the positioning operation.

FIG. 4 schematically shows the process of positioning. In step S1, an image is recorded by the camera 12. In step S2, image processing is effected in the computer 7 (including the comparison with the predetermined nominal position), and in step S3, movement control of the positioning device 4 is then carried out. Thus, positioning can be effected by one single cycle of steps S1-S3. Of course, it is also possible to pass through several cycles of steps S1-S3, as indicated by the arrow P3. This allows stepwise positioning.

Figure 5:
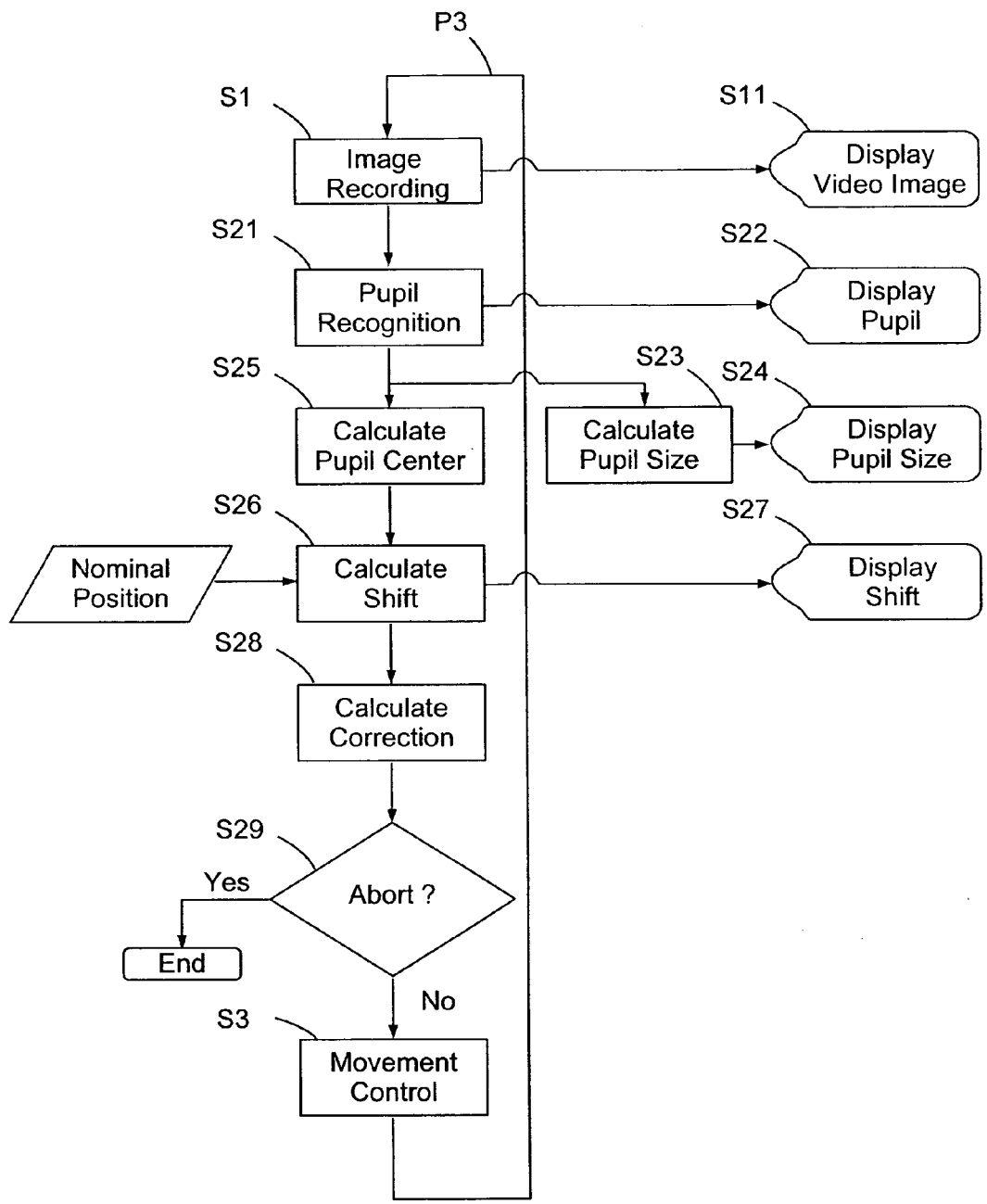
FIG. 5 shows a further flow scheme explaining a modification of the positioning operation.

FIG. 5 shows a modification of the flow scheme of FIG. 4. In step S1, an image is recorded. The recorded image can be displayed on the monitor 9 in step S11. In step S21, the computer 7 effects pupil recognition. The pupil can be displayed on the monitor 9 in step S22. Further, in step S23, the size of the pupil can be calculated and displayed in step S24.

In step S25, which follows step S21, the pupil's center P1 is calculated and is used to calculate the required shift in step S26, taking into consideration the nominal position, which shift can be displayed on the monitor 9 in step S27. The present shift is then used in step S28 to calculate the required correction or movement of the bed 2 relative to the contact glass 10, respectively. If in step S29 no abort is carried out by the surgeon and/or the patient, the movement control is carried out in step S3. Of course, these steps can be repeated several times, as indicated by the arrow P3.

In the embodiments described so far, positioning is carried out automatically, achieving a precision in a lateral position (in a plane parallel to the bed 2) of 50 μm. However, it is also possible, that the surgeon controls the positioning device 4 manually on the basis of the display effected in step S27 and, thus, positions the eye A of the patient at the desired nominal position. Of course, this can be carried out under constant control (i.e. image recorded image and evaluation).

For example, displaying of the shift can be effected by displaying the absolute shift. It is also possible to show to the surgeon that the bed 2 has to be shifted in a particular direction. In this case, no absolute shift is represented, but only a relative shift, namely the shifting direction.

The movement control in step S3 or the entire closed-loop control process of FIG. 4 or 5, respectively, can be stopped automatically when the eye A has been positioned at the nominal position. Of course, it is also possible to stop the closed-loop control process automatically when safety limits are reached or exceeded respectively. For example, the contact pressure of the contact glass 10 on the eye A can be continuously detected, and the interruption can be effected when the pressure is too high. Also, an interruption can be effected if the pupil is outside a capturing region 18 shown in FIG. 3 in the recorded image (a capturing region may have a diameter of, for example, 500 μm). If this is the case, the patient has to be positioned first by manual control of the positioning device 4 such that his pupil 17 is located within the capturing region 18.

Of course, the displaying in steps S11, S22, S24 and S27 need not be effected via the monitor 9, but can also be effected by reflection into the microscope ocular 6. In this case, positioning can thus be effected under visual control through the microscope.

The eye A can be illuminated in order to carry out good recording. For this purpose, as shown in broken lines in FIG. 2, a partially transparent coupling-in mirror 19 can be arranged between the beam splitter 13 and the camera 12, for example, which couples illumination light from an illumination source 20 into the observation beam path 15. The illumination light can be light in the visible spectral range. It is actually also possible to use illumination light from the infrared spectral range. In this case, the camera 12 has to be adjusted, of course, to the corresponding illumination light wavelength.

The described embodiments can be freely combined, as far as it appears reasonable.

Thus, using the detection device 11 an indication concerning the required shift of the eye A relative to the contact glass 10 can be determined, which shift is required to move the eye A to the nominal position. For example, the nominal position can be selected such that the axis of vision of the eye A is centered relative to the contact glass 10 or to the curved contact glass bottom surface, respectively.

Instead of the eye's pupil, any other detectable structure of the patient's eye can be evaluated in the recorded image in order to determine the indication concerning the required shift.

The determined indication (e.g. shifting direction) can be provided to the surgeon or the operator of the ophthalmic apparatus 1, respectively, not only by visual means, but instead or additionally also by acoustic means.

All data transmissions in the ophthalmic apparatus 1, in particular between the camera 12 and the computer 7, as well as between the computer 7 or the treatment device 3, respectively, and the positioning device 4 can be carried out in a wire-connected or wireless manner.

Further, a fixation mark (not shown) can be displayed in the observation beam path 15 for the patient to look at during the positioning operation.

How the laser radiation L for the treatment is generated will be briefly described in connection with FIGS. 6 and 7. Said laser radiation is employed when the eye A of the patient has been positioned at the nominal position by means of the described procedure and has been spatially fixed using the contact glass 10.

Figure 6:
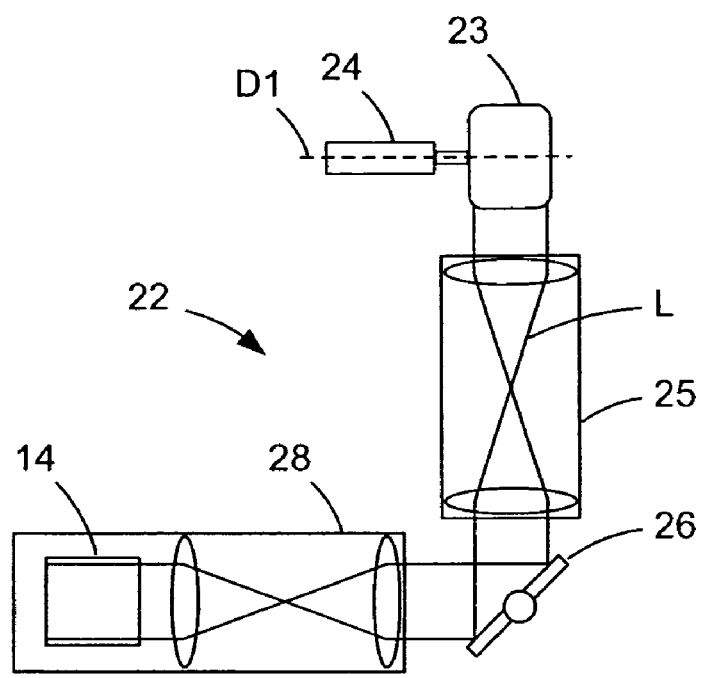
FIG. 6 shows a top view of a laser module for the treatment device 3 of FIG. 1.
Figure 7:
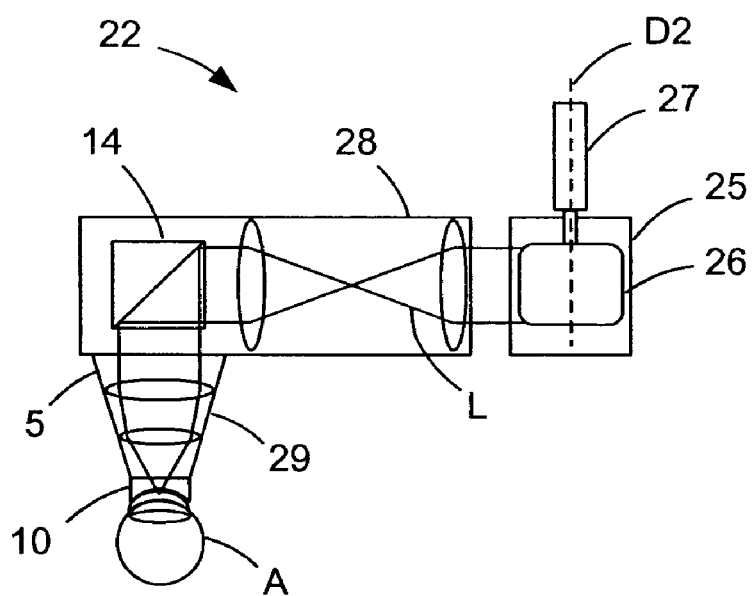
FIG. 7 shows a lateral view of the laser module of FIG. 6.

In order to generate the laser radiation L, a laser module 22 is arranged in the treatment device 3, which laser module 22 is schematically shown in a top view in FIG. 6 and in a lateral view FIG. 7, with FIG. 7 also schematically indicating the patient's eye A to be treated.

The laser module 22 includes a femtosecond laser which emits the desired laser radiation L, as well as expansion optics arranged following the laser, both of which are not shown in the figures for simpler representation. The expansion optics can comprise axially shiftable elements such that the laser focus of the laser radiation can be shifted in an axial direction in the cornea of the eye A.

Arranged following the expansion optics is a first scanning mirror 23 which, driven by a motor 24, is pivotable about a first axis of deflection D1. The first scanning mirror 23 is located in a pupil of a pupil image 25 following the first scanning mirror 23. In a further pupil of the pupil image 25, a second scanning mirror 26 is arranged, which is also driven by a motor 27. The second scanning mirror 26 rotates about a second axis of deflection D2, which is shown in broken lines in FIG. 7.

Arranged following the second scanning mirror 26 are scanning optics 28, in whose pupil the second scanning mirror 26 is located and whose beam path is deflected to the treating head 5 by the beam splitter 14. The treating head comprises focusing optics 29 which focus the laser radiation L via the contact glass 10 in the cornea of the eye A.

The invention claimed is:

1. An ophthalmic apparatus comprising:
    a supporting device for a patient;
    an eye treatment device, which comprises a contact element for spatially fixing an eye of a patient with respect to the treatment device;
    a positioning device for shifting the supporting device and the contact element relative to each other to position the eye, before the eye is fixed using the contact element, at a predetermined nominal position relative to the contact element, the positioning device having a precision in lateral positioning of about fifty μm; and
    a detection device, which records a recorded image of the eye of the patient present on the supporting device and, on the basis of said recorded image, determines a first determined indication concerning a first relative shift of the supporting device with respect to the contact element, the first relative shift being required to move the eye toward the predetermined nominal position by movement of the positioning device.

2. The apparatus as claimed in claim 1, wherein the detection device records a further image of the eye during or after the first relative shift effected by the positioning device or during or after part of the first relative shift and, on the basis of said further recorded image, determines second determined indication concerning a second relative shift of the supporting device with respect to the contact element, the second relative shift being required to move the eye toward the nominal position by movement of the positioning device.

3. The apparatus as claimed in claim 2, wherein the positioning device causes a relative shift of the supporting device with respect to the contact element on the basis of at least one of the first or second determined indication(s).

4. The apparatus as claimed in claim 1, wherein the positioning device causes the first relative shift while the contact element is in contact with the eye.

5. The apparatus as claimed in claim 2, further comprising a signaling unit that signals to an operator of the ophthalmic apparatus, on the basis of at least one of the first determined indication and the second determined indication, how the positioning device is to be controlled in order to move the eye to the nominal position.

6. The apparatus as claimed in claim 1, wherein the detection device determines at least one of the first determined indication concerning the first relative shift and second determined indication of the second relative shift on the basis of the position of the eye's pupil in the recorded image.

7. The apparatus as claimed in claim 1, wherein the detection device further comprises an illumination source, which emits illumination radiation by which the eye is illuminated for recording.

8. The apparatus as claimed in claim 1, wherein the treatment device spatially fixes the eye, located at the nominal position, by contact with the contact element.

9. The apparatus as claimed in claim 2, wherein the detection device determines at least one of the first determined indication concerning the first relative shift or second determined indication of the second relative shift by deriving an actual position of the eye from the recorded image of the eye or the further recorded image of the eye, comparing the actual position with the nominal position, calculating the required first relative shift or second relative shift and deriving said first indication or second indication from the required first relative shift or second relative shift respectively.

10. An ophthalmic method for positioning an eye of a patient at a predetermined nominal position relative to a contact element of an eye treatment device, comprising
    recording an image of a patient's eye;
    determining a first indication concerning a first relative shift of the patient with respect to the contact element on the basis of the recorded image, said first relative shift being required to move the eye toward the nominal position, and effecting the first relative shift with a precision in lateral positioning of about fifty μm on the basis of said indication or providing an operator of the eye treatment device said indication.

11. The method as claimed in claim 10, further comprising recording a further image of the eye during or after the first relative shift or part of said first relative shift;

determining a second indication concerning a second relative shift of the patient with respect to the contact element on the basis of said further recorded image, said second relative shift being required to move the eye toward the nominal position; and effecting the second relative shift on the basis of said second indication concerning the second relative shift or providing the second indication concerning the second relative shift to an operator of the eye treatment device.

12. The method as claimed in claim 10, wherein effecting at least one of the first relative shift or the second relative shift takes place while the contact element is in contact with the eye.

13. The method as claimed in claim 10, further comprising signaling to an operator, on the basis of the determined indication(s), how to control a positioning device for shifting the patient and the contact element relative to each other so as to move the eye toward the nominal position.

14. The method as claimed in claim 10, further comprising spatially fixing the eye once it is located at the nominal position.

15. The method as claimed in claim 10, further comprising determining at least one of the first indication concerning the first relative shift and second indication concerning the second relative shift on the basis of the position of the eye's pupil in the recorded image.

16. The method as claimed in claim 10, further comprising:
determining at least one of the first indication concerning the first relative shift and second indication concerning the second relative shift by deriving the actual position of the eye from the recorded image of the eye;
comparing the actual position with the nominal position; and
calculating a required shift therefrom and deriving the indication from said required shift.

* * * * *

UNITED STATES PATENT AND TRADEMARK OFFICE
CERTIFICATE OF CORRECTION

| | | |
|---|---|---|
| PATENT NO. | : 8,292,432 B2 | |
| APPLICATION NO. | : 12/513767 | |
| DATED | : October 23, 2012 | |
| INVENTOR(S) | : Mark Bischoff et al. | |

It is certified that error appears in the above-identified patent and that said Letters Patent is hereby corrected as shown below:

In the Specification

Col. 3, line 59, delete "wire" and insert --wired--

Col. 4, line 42, delete "discloses" and insert --disclose--

Col. 5, line 34, after "glass 10", insert the following paragraph:

--The recorded image of the eye A is evaluated in the computer 7 to allow control of the positioning device 4 such that the bed 2 and, thus, the eye A of the patient present on the bed 2 can be moved to a predetermined nominal position relative to the contact glass 10.--

Signed and Sealed this
Tenth Day of February, 2015

Michelle K. Lee
*Deputy Director of the United States Patent and Trademark Office*